United States Patent [19]

Dahms

[11] Patent Number: 5,179,024
[45] Date of Patent: Jan. 12, 1993

[54] SEALED VIALS CONTAINING IMPROVED KARL FISCHER SOLUTIONS, AND PROCESS FOR WATER DETERMINATION USING THESE VIALS

[76] Inventor: Harald Dahms, 472 Madison Ave., Toms River, N.J. 08753

[21] Appl. No.: 707,684

[22] Filed: May 30, 1991

[51] Int. Cl.$^5$ .................... G01N 21/78; G01N 33/18
[52] U.S. Cl. ................................ 436/42; 422/58; 422/61; 422/102; 436/165
[58] Field of Search ............... 436/42, 163, 164, 165; 422/58, 61, 75, 102

[56] References Cited

U.S. PATENT DOCUMENTS

| | | | |
|---|---|---|---|
| 2,780,601 | 2/1957 | Blomgren et al. | 436/42 |
| 2,967,155 | 1/1961 | Blomgren et al. | 436/42 |
| 3,528,775 | 9/1970 | O'Hara et al. | 422/61 |
| 3,634,038 | 1/1972 | Rampy | 23/253 R |
| 3,682,783 | 8/1972 | Dahms et al. | 436/42 X |
| 4,005,983 | 2/1977 | Dahms | 23/230 R |
| 4,332,769 | 6/1982 | Rampy et al. | 422/75 |
| 4,378,972 | 4/1983 | Scholz | 436/42 |
| 4,537,747 | 8/1985 | Castaneda | 422/100 |
| 4,596,780 | 6/1986 | Castaneda | 436/176 |
| 4,619,900 | 10/1986 | Scholz | 436/42 |
| 4,720,464 | 1/1988 | Kuwata et al. | 436/42 |
| 4,725,552 | 2/1988 | Dahms | 436/42 |
| 4,786,602 | 11/1988 | Dahms | 436/42 |
| 4,802,957 | 2/1989 | Kuwata et al. | 436/42 X |

FOREIGN PATENT DOCUMENTS

| 0027650 | 3/1981 | Japan | 436/42 |
|---|---|---|---|
| 0247955 | 11/1986 | Japan | 436/42 |

Primary Examiner—Robert J. Hill, Jr.

[57] ABSTRACT

An improved K.F. solution for colorimetric analysis to determine the water content of an unknown sample, and an improved sealed vial or ampule containing this solution and a process for determining water content using this solution and the sealed vial. The ampule is designed so that it can be broken into discrete parts, where an air-tight seal is maintained by the presence of an elastic band located in the area where the vial is broken. A syringe needle is used to pierce the elastic band to inject a precisely controlled amount of unknown sample into the vial. The K.F. solution is optimally comprised of a reducing ion such as $SO_2$, a buffer including imidazole or its derivatives, iodine, iodide, and a solvent which can include a halogenated hydrocarbon.

31 Claims, 1 Drawing Sheet

SEALED VIALS CONTAINING IMPROVED KARL FISCHER SOLUTIONS, AND PROCESS FOR WATER DETERMINATION USING THESE VIALS

FIELD OF THE INVENTION

This invention relates to improvements in the determination of water content in samples using colorimetric analysis, and more particularly to an improved disposable vial used in such determinations, reagents that are particularly advantageous when used with said vials, and processes utilizing said improved vials and reagents for the colorimetric determination of water content by Karl Fischer methods.

BACKGROUND ART

The determination of water content is important in many commercial products. For example, minute quantities of water in chemical process streams are detrimental for certain reactions. Further, the electrical properties of insulators are strongly dependent on water traces, and the water content of fluids such as gasoline has to be kept below a certain level. From these few examples, it is apparent that water determinations are among the most frequently performed analyses in many laboratories.

The currently most widely practiced water determination method is the "Karl Fischer" method, named after its originator who described the basis of this method in "Zeitschrift Fuer Angewandte Chemie", volume 48, p. 394–396 (1935). In this method, a sample containing an unknown amount of water is added to a Karl Fischer reagent, hereinafter denoted K.F. reagent. This reagent is usually a solution of iodine and a reducing ion (sulfur dioxide) in a buffer (such as pyridine or amines), and methanol or other solvents.

Due to the presence of iodine in the K.F. reagent its color is brown. When an unknown sample of water is added to the K.F. reagent, the iodine is consumed so that the dark brown color of the iodine in the "fresh" reagent disappears, changing to a light yellow color of the "spent" reagent. In a typical water determination by the Karl Fischer method, a water-containing sample is injected into a prepacked volume of K.F. reagent and the change in optical absorbance of the K.F. reagent is measured. The change in optical absorbance can be transformed by an electrical circuit into a direct readout of water content of the sample. This technique gives immediate quantitative results irrespective of the fading of strength of the K.F. reagent during storage.

An example of a reaction vessel for holding a K.F. reagent used in colorimetric analysis is that shown in U.S. Pat. No. 4,005,983. The vial of this reference includes a generally cylindrical shaped tube having an opening at one end which is covered by a liner held by a screw cap. An opening is provided in the screw cap for insertion of a syringe needle through the elastic liner. This allows entry of a sample into the vial while not exposing the K.F. reagent within the vial to the atmosphere. An electrical circuit is provided which compensates for the dilution effect that occurs when a sample volume is added to the prepacked K.F. reagent in the vial.

While the vial described in the aforementioned patent has many advantages, it does not solve all of the problems encountered in this technology. For example, the K.F. reagents prepacked in these vials have to remain in the vials for long periods of time, extending for many months and even years, prior to use. This places difficult burdens on both the inherent stability of the K.F. reagents and the design of the vial itself. Since the intrusion of even micrograms of moisture from the atmosphere will render useless the K.F. reagent contained therein, the vial must provide perfect sealing for very long periods of time. It has been found that the vials of U.S. Pat. No. 4,005,983, while providing adequate sealing for a few months, do not provide prolonged sealing sufficient to prevent all moisture from contacting the enclosed K.F. reagents.

Another requirement of the vial is that there must be easy access to the interior of the vial without, as noted above, exposure of its contents to the atmosphere. While the vials of U.S. Pat. No. 4,005,983 allow easy introduction of the sample, they do not provide the proper sealing, primarily due to leakage through and around the plastic septum (liner) used to seal the open end.

In water determination by colorimetric K.F. analysis, many variations can arise which will impact the accuracy of the result. For example, when a sample is added a dilution effect occurs. It is important that the dilution effect result in a predictable and uniform absorbance change. In addition to this dilution effect, the optical absorbance technique used for colorimetric K.F. analysis yields results which are dependent on the nature of the vials or containers that are used, the unknown properties of the added sample, and the inaccuracies produced by the use of glass or other types of transparent containers. For example, the walls of the containers in which the K.F. reagent-sample reaction occur are not generally optically perfect. This means that the second optical reading, after the addition of the unknown sample, may be changed by a difference in properties of the glass walls of the containers. Also, the optical properties of the added unknown sample, such as its optical density, refractive index, etc. are unknown at the time the sample is added to the reagent-containing vessel. Again, this will cause a change in the second optical absorbance reading which could render it inaccurate. Still further, another factor which impairs the accuracy of this technique is that containers are generally cylindrical vessels. Optical readings through these vessels are more complex than through perfectly rectangular optical containers. In order to address these variations which could lead to inaccurate results, a technique was proposed for colorimetric determination of water content using Karl Fischer reagents where the method involved using two different wavelengths for analysis. This approach is described in U.S. Pat. No. 4,786,602, wherein a small amount of a dye solution is included in the prepacked volume of K.F. reagent in the container. This dye was chosen to be one having its maximum absorption at a wavelength which is different than the wavelengths that are optically absorbed by iodine. Optical absorption measurements are made on the solution including both the K.F. reagent and the dye at two different wavelengths. These two different wavelengths are also used after the unknown sample is added to the K.F. reagent. Use of the second wavelength allows a correction for the reading determined by the first wavelength in order to compensate for the various factors causing inaccuracy in colorimetric K.F. water determination.

While the approaches described hereinabove have led to improved accuracies in colorimetric Karl Fischer water determination, additional improvements need to be made. For example, it is desirable to provide an improved vial in which a known amount of Karl Fischer reagent can be stored for an indefinite amount of time, where the vial is one which is easy to use for insertion of the unknown sample and which provides a perfect seal for an extended period of time prior to its use. Further, many existing vial designs do not allow entry of a predetermined precise amount of sample, where the sample volume is extremely small. This can impose an additional burden on the vial design since a substantially perfect seal also must be provided before, during and after introduction of the unknown sample into the vial. The prior vial designs (with the exception of that described in U.S. Pat. No. 4,005,983) utilize ratios of sample: reagent of at least 5:1. In contrast with that, the sample: reagent ratio in the vials of the present invention are less than about 1:4. Vacuum and capillary action to introduce the sample are not suitable for very small sample amounts.

Accordingly, it is an object of this invention to provide an improved vial that can be used for the colorimetric determination of water content by the Karl Fischer technique.

It is another object of this invention to provide an improved vial having a predetermined amount of Karl Fischer reagent therein, where the vial provides excellent sealing against an ambient atmosphere of any type, before, during and after introduction of the unknown sample into the vial.

While it is important to provide a vial providing excellent sealing before, during and after entry of the sample therein, it is also important to provide a vial into which the sample can be introduced in precisely determined amounts. It is sometimes preferable that the burden of limiting the amount of sample introduced into the vial not be placed on the vial itself.

Thus, it is another object of the present invention to provide an improved design of a vial useful for a colorimetric determination of water content by the Karl Fischer method, in which the sample is readily introduced into the vial in predetermined amounts not directly determined by the vial design.

It is another object of this invention to provide an improved vial useful in colorimetric K.F. water determination where a predetermined amount of unknown sample is easily introduced into the vial.

In addition to the requirements on the vial, described above, it is also advantageous to provide improved K.F. reagents which are particularly adapted to the Karl Fischer determination of water content by colorimetric analysis. Prior to the present invention, there has been little effort to define Karl Fischer reagents which would be particularly suitable for colorimetric analysis. It is recognized, however, that many different reagents have been used for Karl Fischer determinations, and in particular for coulometric analysis techniques. However, the art has not focussed on the development of reagents which will yield linear changes of absorbance when adding water, or reagents which will provide predictable and uniform absorbance changes when the solution is diluted by the addition of the unknown sample. In the present invention, it has been found that the addition of particular additives in selected amounts will provide reagents that are advantageous for colorimetric analysis via the Karl Fischer technique, and are particularly suitable for use in the vials of this invention. These reagents provide linear changes with the water content of the unknown sample and also very controlled and uniform changes in optical absorbance due to the dilution effect that occurs when a volume of sample is added to the reagent.

Thus, it is another object of my invention to provide improved reagents for the K.F. determination of water by colorimetric analysis.

It is another object of my invention to provide improved reagents useful for the colorimetric analysis of water content using the Karl Fischer technique, where these reagents are used with the improved vials described hereinabove.

It is another object of my invention to provide a sealed, improved vial having contained therein a prepacked volume of the improved K.F. reagents of this invention.

It is another object of my invention to provide a process for K.F. determination of water content in an unknown sample using colorimetric analysis involving the use of improved reagents in vials described herein.

In Karl Fischer analysis for water determination titrimetric methods are commonly used wherein the K.F. reagent is a monocomponent reagent or a bicomponent reagent. In the first instance, the sample is titrated with a solution which contains a reducing ion such as $SO_2$, a buffer such as pyridine or an amine, iodine, and an alcohol such as anhydrous methanol. Due to stability problems with extended storage, a bicomponent reagent is typically used wherein the vessel solution contains sulfur dioxide and pyridine in methanol while the titrant contains iodine in methanol. Examples of reagents suitable for titrimetric determinations of water are described in U.S. Pat. No. 4,378,972 wherein several amines can be used.

While there are many reagents known in the art for use in titrimetric determinations of water using the Karl Fischer method, there has been relatively little effort to develop reagents that are particularly suitable for colorimetric determinations of water content using the Karl Fischer method. Reference is made to U.S. Pat. Nos. 3,723,062 and 4,786,602 for a description of K.F. reagents previously used for colorimetric determinations of water content.

Colorimetric water determination is quite different from titrimetric water determination and it is apparent to those of skill in this art that the teachings from one technique cannot be automatically applied to the other technique. For example, many of the reagents used for titrimetric water determinations cannot be used for colorimetric water determinations. For example, as will be described later, the iodine content of a colorimetric reagent is preferrably an order of magnitude less than it is in a titrimetric solution.

Thus, it is a further object of this invention to provide improved and new reagents for colorimetric determination of water content using the Karl Fischer analysis.

It is another object of this invention to provide improved reagents for colorimetric determination of water content by the Karl Fischer method, where the reagents have improved optical properties.

It is another object of the present invention to provide a combination including a sealed vial of a particular design having therein a Karl Fischer reagent that can be used for colorimetric analysis of water content.

It is a further object of this invention to provide a process for colorimetric determination of water content using a sealed vial of a particular design having therein an improved colorimetric K.F. reagent.

SUMMARY OF THE INVENTION

This invention provides an improved vial for colorimetric analysis of water content using the Karl Fischer reaction, improved reagents for use in said vial, and improved processes using said vial and said reagents.

The vial is generally tubular in shape and includes a portion of substantially constant cross section around which a scored mark is made. Due to the application of pressure, the vial will break into two parts along the scored line. An elastic enclosure is in contact with the vial in the vicinity of the scored line, and serves to maintain an airtight seal while holding the two portions of the vial when the vial is broken. The elastic member is somewhat "bunched" in the area of the scored mark so that the two broken portions of the vial will not be held in perfect contact after the break is made. This allows a small space between the two broken portions of the vial. The unknown sample is contained in a syringe which is used to pierce the elastic enclosure in the area of the separation between the two portions of the broken vial. A fixed amount of unknown sample can be introduced into the vial in this manner. In this design, the amount of unknown sample introduced into the vial is determined by the syringe and not by the vial design. Further, the elastic enclosure provides a substantially perfect seal even though the broken parts of the vial can be separated from one another to allow entry of the syringe needle into the vial.

The reagents used for colorimetric Karl Fischer analysis in accordance with this invention have specialized optical properties not found in K.F. reagents typically used in a titration mode of analysis. The colorimetric reagents include a reducing ion such as $SO_2$, a buffer such as imidazole, iodide, iodine, and a solvent which can include at least 20% by volume of a halogenated hydrocarbon containing 1-3 carbon atoms, where the halogens are chlorine, bromine, and iodine. A typical halogenated hydrocarbon is chloroform. The remaining portion of the solvent can be an alcohol, such as methanol. In the practice of the present invention, the reagent is placed in the vial which is then sealed. A first optical absorbance measurement is made using the appropriate wavelength. The sealed vial is then broken along the score mark to provide two portions that are separate from one another but wherein an airtight seal is maintained due to the elastic enclosure. A known amount of sample is then injected through the elastic enclosure into the vial. A second optical absorbance measurement is made to determine the decrease in absorbance due to the introduction of the water-containing sample. The water content of the sample is then determined based on the decrease in optical absorbance. As will be pointed out later with more particularity, the use of this sealed vial and these improved reagents provide numerous advantages which cannot be obtained using other reagents in a colorimetric Karl Fischer analysis.

These and other objects, features, and advantages will be more apparent from the following more particular description of the preferred embodiments.

BEST MODE FOR CARRYING OUT THE INVENTION

Figure 1:
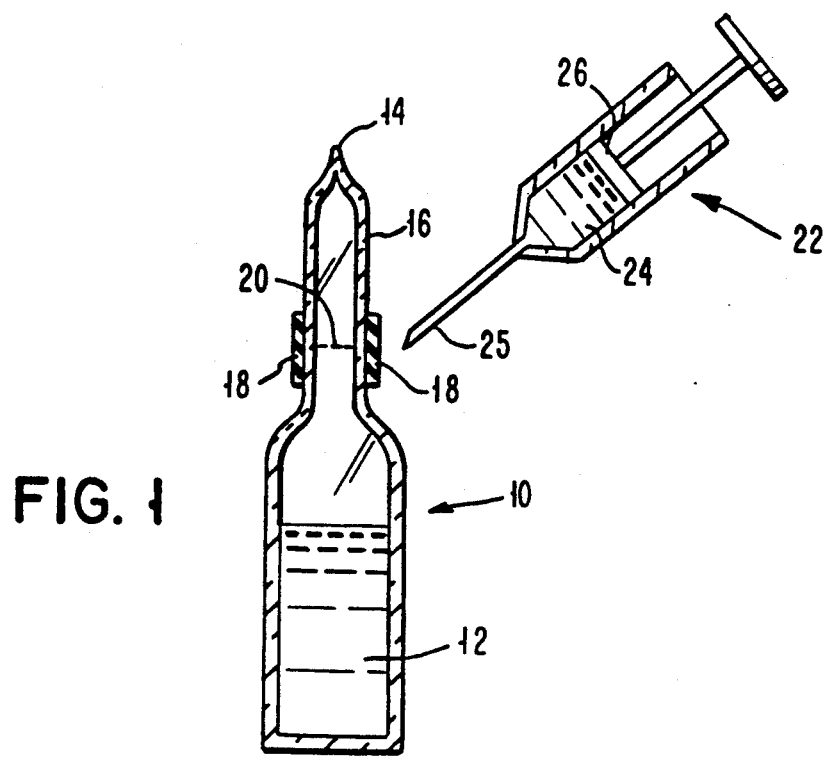
FIG. 1 schematically illustrates an improved reagent vial in accordance with the present invention, while FIG. 2 indicates the injection of a sample having an unknown water content into the vial.

FIG. 1 indicates a vial or ampule 10 which contains the K. F. solution 12 of this invention. Ampule 10 is sealed at end 14. Located around a portion 16 of generally uniform diameter is an elastic enclosure 18. Ampule 10 has a scoremark 20 to facilitate the breaking of ampule 10 into two parts prior to the introduction of a sample therein.

Ampule 10 is typically made of glass, but other materials can also be used including plastics. The exact shape of the ampule is not critical, although most suitable ampules will be generally cylindrical in cross section. As will be seen later it is desirable that the portion 16, where the scoremark 20 is located, be of a uniform diameter to ensure that the elastic enclosure means 18 fits tightly against portion 16. Also, the gas phase may be flushed with an inert gas (such as argon, nitrogen, helium, etc.) prior to sealing ampule 10 in order to prevent reaction of the contents 12 with air present in the ampule. The elastic band 18 is typically a tubular piece of silicone rubber tubing. It will bend when the ampule is broken along the scored line 20 without breaking or admitting the atmosphere into the ampule. The uniform diameter of vial 10 in the vicinity of the score mark 20 ensures that the elastic 18 will maintain an airtight seal when the vial is broken, and will not slip from its position.

Figure 2:
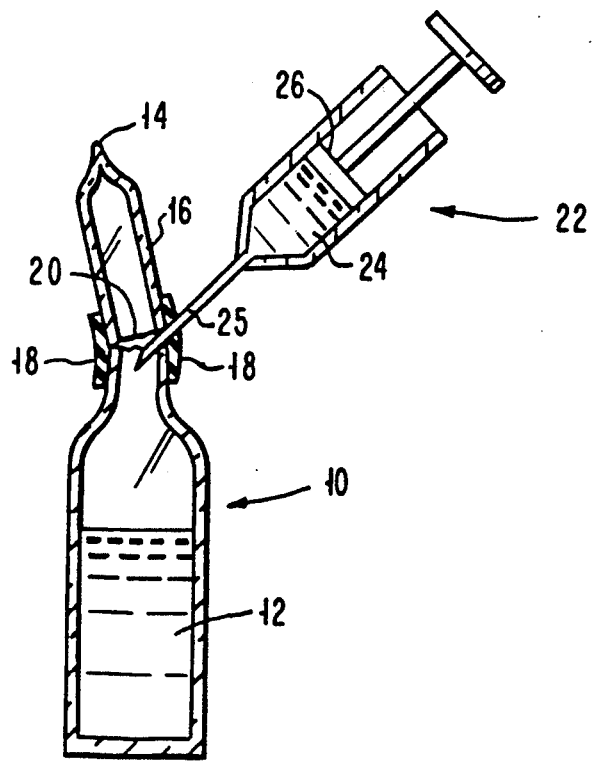

FIG. 2 illustrates the breaking of the top portion of the ampule 10 and the introduction of a sample of unknown water content into the ampule. For this purpose, syringe 22 is used where the amount of sample 24 delivered by the syringe can be determined with great accuracy. In operation, a slight sideward pressure will cause the top portion of ampule 10 to break away from the bottom portion of the ampule along the scoremark 20. The elastic tubing 18 will prevent the introduction of the atmosphere into ampule 10 even though the two broken portions of the ampule are separated from one another. This allows the syringe needle 25 to be easily injected through the elastic band 18 into the center of the vial. Piston 26 is then pushed forward to discharge a measured amount of sample 24 into the vial. Thus, in this arrangement a very precise and reproducible amount of sample can be introduced into the vials, the design of the vial having no effect on the amount of sample to be introduced.

A slight degree of vacuum inside ampule 10 will tighten the rubber tubing seal 18 when the ampule is broken, by pulling the rubber tubing inwardly. This helps to create a gap between the two broken portions of the ampule.

Thus, when the sample is to be introduced by piercing the elastic band 18, the syringe needle can easily pierce elastic tubing 18 and enter the vial through the gap between the broken parts. It has been found that the best inside pressure is in the range from slightly below atmospheric pressure (98% of atmospheric pressure) to a vacuum of about 60% of atmospheric pressure.

It also appears to be advantageous to "prestress" the rubber seal 18. This is accomplished by bunching the rubber in the vicinity of the scoremark 20. This helps to create a gap between the broken portions of ampule 10 when the ampule is broken.

In operation, ampule 10 is partly filled with the K. F. solution of this invention. The ampule is then sealed and elastic band 18 applied as shown in FIG. 1. This sealed ampule is then stored and delivered to the user. When it is to be used its optical absorbance is measured at a wavelength typically at about 450–550 nanometers. The apparatus for such optical absorbance measurements, a colorimeter or spectrophotometer, is well known in the art. The initial optical absorbance is labelled A1.

The next step is to break the top of the neck 16 of the ampule by bending it sideways until a break is caused along the scoremark 20. Elastic means 18 protects the opening which is created. The syringe needle 25 then pierces through elastic means 18 and a measured amount of sample is injected into ampule 10 from the syringe 22. The syringe is then withdrawn and the broken ampule, containing the unknown sample and the K. F. solution, can be inverted to mix the sample and the solution 12. During this mixing, elastic means 18 prevents the contents from spilling from ampule 10 and also prevents contact of the ampule contents with the atmosphere. After mixing the optical absorbance is again measured to yield a different value A2. This second value will be lower than the initial optical absorbance A1 because of the disappearance of iodine according to the K. F. reaction $$H_2O + I_2 + SO_2 = 2HI + SO_3$$

The amount of water present in the sample can now be calculated according to $$\text{water amount} = K\left[A1 - A2\frac{(V_0 + V_s)}{V_0}\right] \quad (1)$$

where K is a constant known through calibration,
A1 is the optical absorbance of the K. F. solution prior to adding the sample,
A2 is the optical absorbance of the ampule contents after adding the unknown sample.
$V_o$ is the volume K. F. solution in the ampule,
$V_s$ is the volume of the unknown sample added to the ampule.

Another approximate formula for the water content of the unknown sample is the following $$\text{water amount} = K\left[\frac{V_0 A1}{V_0 + V_s} - A2\right] \quad (2)$$

Equation 2 is an approximation, the determination in accordance with equation 1 being the precisely accurate amount. Equations 1 and 2 are easily performed on a computer controlled colorimeter.

The constant K is determined by analyzing numerous samples of known water content with the method of this invention. By knowing the amount of water, $V_s$, $V_o$ and the measured A1 and A2, equation (1) can be solved for K and the average of the found K is thereby established for use with unknown samples.

K. F. Solution

As noted previously, most of the K. F. solutions being used commercially have been designed for titrimetric analysis. However, these solutions are generally unacceptable for precise measurements when colorimetric analysis is used, and several of these titrimetric solutions simply cannot be used for colorimetric analysis. Based on considerable experimentation, it has been found that the following reagents provide superior optical properties lending themselves to use for colorimetric analysis, and particularly where such reagents are used together with a sealed vial that can be stored for considerable amounts of time and delivered to the user without adverse degradation and loss of optical properties.

For colorimetric measurements of water content, the change of optical absorbance per added unit of water has to be as constant as possible. It is desirable that the change in optical absorbance should be linear over a wide range in the amount of water added by the unknown sample. That is, the optical absorbance should decrease by the same amount per unit of water added. It has been found that the K. F. solution, being comprised of a reducing ion such as $SO_2$, a buffer, iodine, and a solvent is more superior for colorimetric analysis when imidazole is present in a range of about 0.001–4.5 moles per liter of solution. In the practice of this invention, the K. F. solution contains imidazole or its derivatives in the specified range. Other amines, known for use in titrimetric solutions, cannot be used. Derivatives of imidazole that may be used in this invention are, for example, 1-methylimidazone or 2-propylimidazole and in more general terms compounds of the formula

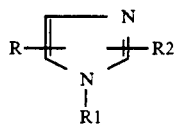

in which R, R1 and R2 are each a hydrogen, an alkyl group or a phenyl group, in any combination in any order.

Based on considerable experimentation, it has been found that the addition of iodide also improves the accuracy of the optical absorbance measurement. These experiments have shown that optical absorbance change per water addition, for a fixed amount of water, becomes very constant when iodide is present in the K. F. solution in an amount at least about 0.003 moles per liter. While iodide has been used in titrimetric solutions of the two component type, there has been no suggestion that the presence of iodide in a one part K. F. solution would be advantageous for colorimetric analysis. Thus, the K.F. solutions of the present invention include both iodide (I−) and iodine ($I_2$) in the initial solution present in ampule 10. While amounts of iodide in excess of about 0.003 moles per liter of solution will provide very constant change in absorbance per added unit of water, the amount of iodide can be as little as about 0.002 moles per liter while still providing a beneficial effect.

It should be noted that the range of iodine concentration used in the present invention is different from that used in prior titration methods. While the strength of titration solutions is usually above 0.05 moles of iodine per liter, the strength of all colorimetric solutions of the present invention is below 0.02 moles of iodine per liter. More typically, the colorimetric solutions are below a strength of 0.005 moles of iodine per liter which is at least one order of magnitude below the iodine strength of titration solutions. Thus, no meaningful relationship can be inferred from the behavior of those titration solutions.

It has also been found that, in this range of low iodine concentration for colorimetric applications (iodine concentration below 0.02 moles per liter), certain ratios of concentrations give best results. These ratios are at least partially unknown in conventional Karl Fischer reagents used for titration purposes.

The ratio of molar concentrations of sulfur dioxide to that of imidazole and its derivatives is preferably between 0.95:1 and 0.005:1. (Iodine concentration below 0.02 moles per liter.)

The ratio of molar concentrations of sulfur dioxide to that of iodine is preferably between 3:1 and 3:0.001. (concentration of $I_2 < 0.02M$).

These ranges are partially outside those of Karl Fischer reagents previously described in the art.

Furthermore, the ratio of molar concentrations of iodide to that of iodine is preferably between 3:0.95 and 3:0.0001. (concentration of $I_2 < 0.02M$).

The K. F. solutions of this invention also contain a solvent for the reactants of the K. F. solution. The solvent is typically an anhydrous low molecular weight alcohol, preferably methanol or ethyleneglycol monomethyl ether. Since the K. F. solution gets diluted when the sample is added, it is particularly significant for accurate results that the dilution by addition of the sample results in predictable optical absorbance changes. That is, when the volume of the ampule contents changes from 5 to 6 milliliters, the resulting absorbance change should be 5/6 of the original optical absorbance. It has been found that the addition of more than about 20% by volume to K. F. solutions of halogenated hydrocarbons can provide very accurate compensation for dilution effects. These additions are halogenated hydrocarbons containing 1-3 carbon atoms which are partially or fully halogenated, the halogens being chlorine, bromine, and iodine. Particularly, suitable examples include chloroform, bromoform, 1,2 dichloroethane, trichloroethylene, and iodomethane.

Thus, a representative K. F. solution in accordance with the present invention is one comprised of $SO_2$, imidazole, iodine in an amount less than about 0.02 moles per liter, iodide, and a solvent optionally including at least 20% by volume of a halogenated hydrocarbon. Iodide is present in an amount of at least 0.002 moles per liter, while the imidazole is present in an amount of about 0.001-4.5 moles per liter. These reagents have superior optical properties making them advantageous for use in colorimetric water determinations in accordance with the Karl Fischer analysis, and have further particular advantages when used with the sealed ampule represented by FIG. 1. Specific examples of K. F. colorimetric solutions in accordance with the present invention are as follows:

EXAMPLE 1

136 grams imidazole (2 moles) are dissolved in a mixture of 500 milliliters water-free methanol and 500 milliliters chloroform. 45 grams sulfur dioxide (0.7 moles) are then added, followed by 5.6 grams iodine. Small amounts of water are then added which will react according to the Karl Fischer reaction to convert iodine to iodide until the solution contains 2 millimoles of iodine and 40 millimoles of iodide. This solution is now filled in quantities of 5 milliliters into glass ampules of the type shown in FIG. 1 which have a total capacity of 7 milliliters, i.e., 2 milliliters is air space. The tip of the glass ampule is immediately sealed by means of a torch so that the contents are protected from the atmosphere. A piece of silicone tubing is slid over the score mark of the ampule which is now ready for use in a colorimetric water determination.

EXAMPLE 2

24 grams of sulfur dioxide are dissolved in 900 grams of ethylene glycol monomethylether while maintaining the mixture at room temperature by cooling. 68 grams of imidazole are added. 8.4 grams of iodine are then dissolved and small traces of water are added until the iodine concentration is decreased to 2 millimoles by converting the bulk of the iodine to iodide by means of the Karl Fischer reaction. 5 milliliter quantities of this solution are then sealed into glass ampules as described in Example 1.

EXAMPLE 3

700 milliliters of methanol and 300 milliliters of trichloroethane are mixed and 34 grams of imidazole, 22.4 grams sulfur dioxide and 5.6 grams of iodine are added to the solution, one after the other. Small traces of water are added until the iodine concentration is decreased to 500 milligrams iodine by means of the Karl Fischer reaction and the solution contains about 0.04 moles iodide per liter. Quantities of 5 milliliters of this solution are sealed into glass ampules as described in Example 1.

While less preferable the colorimetric Karl Fischer analysis for water content may also be used in the following way: a known volume of Karl Fischer reagent with a known iodine content is sealed into the glass ampule as described previously. For example, 1 milliliter of Karl Fischer reagent with a strength of 1 milligram water per milliliter is sealed in the ampule. The user may now proceed in two ways: he may fill a syringe with a known amount of unknown sample, say 1 milliliter. He then breaks the ampule as usual and injects all of the sample. If the contents of the ampule, after mixing, stay brown he knows that the water content of his sample is below 1 milligram of water per milliliter. If the contents change to colorless he knows that his sample contains more than 1 milligram water per milliliter. He thus knows if the sample is "wet" or "dry", i.e. above or below a certain limit important to him. In an alternative way he may fill a graduated syringe, say a 5 milliliter syringe, with the unknown sample. After breaking the seal of the ampule and inserting the needle of the syringe he now proceeds to introduce small amounts of the sample into the vial filled with the known amount of Karl Fischer reagent until the color of the reagent changes from brown to colorless. He then notes the amount of sample introduced up to this point. If, for example, he used 2 milliliters of sample he knows that his sample contains 0.5 milligram of water per milliliter (1 milliliter of K.F. reagent was in the ampule).

It should be noted that many of the improvements described in this invention, such as the airtight seal of the ampule before and after breaking, the stability of the reagent, etc. are also needed in the mode of operation described in the previous paragraph. However, the feature of the iodine concentration being less than 0.02 millimoles per milliliter, may not be necessary.

It is also to be understood that other methods of introducing known amounts of sample into the vial may be used together with these alternative modes of operation.

While the invention has been described with respect to particular embodiments thereof, it will be apparent to those of skill in the art that some variations can be made therein without departing from the spirit and scope of the invention. For example, the ampule 10 can have a different geometry than that shown, and can be comprised of materials other than glass, although glass is clearly preferable. Further, the principles of applicant's U.S. Pat. No. 4,786,602, wherein a dye is included in a colorimetric K.F. solution, can be incorporated in the solution of the present invention. Other alternatives can include, for example, the use of other solvents in combination with the halogenated hydrocarbons described hereinabove, and the use of reducing ions other than $SO_2$.

I claim:

1. An all-glass sealed vial or ampule containing a Karl Fischer solution for colorimetric analysis of the water content of a sample to be introduced therein, such solution being comprised of a reducing ion, a buffer including imidazole or its derivatives, iodine in an amount less than 0.005 moles per liter, iodide, and a solvent.

2. The vial or ampule of claim 1, where said reducing ion is $SO_2$.

3. The vial or ampule of claim 1, where said solvent includes a halogenated hydrocarbon containing 1-3 carbon atoms partially or fully halogenated, where the halogen is selected from the group consisting of chlorine, bromine, and iodine.

4. The sealed vial or ampule of claim 3, where halogenated hydrocarbon is present in an amount at least about 20% by volume of said Karl Fischer solution.

5. The sealed vial or ampule of claim 3, where said solvent also includes an anhydrous, low molecular weight alcohol.

6. The sealed vial or ampule of claim 5, where said alcohol is selected from the group consisting of methanol and ethyleneglycol monomethyl ether.

7. The sealed vial or ampule of claim 1, where said imidazole or its derivatives is present in an amount about 0.001-4.5 moles per liter in said Karl Fischer solution.

8. A process for the colorimetric determination of the water content of a sample, comprising the steps of:
providing a sealed vial having a first section of approximately constant diameter including a scoremark and an elastic enclosure means surrounding said first section in the vicinity of said scoremark, said vial being sealed and containing a Karl Fischer solution therein of volume $V_0$, said solution including a reducing ion, alcohol, imidazole or its derivatives, iodine in an amount less than about 0.02 moles per liter, and iodide,
measuring a first optical absorbance A1 of said Karl Fischer solution,
breaking said vial along said scoremark to produce discrete pieces,
injecting a sample volume $V_S$ of unknown water content into said vial by a syringe whose needle penetrates said elastic means and passes through a separation between said discrete broken pieces of said vial,
mixing said sample and said Karl Fischer solution in said vial, said elastic enclosure means substantially preventing the contents of said vial from being exposed to the atmosphere,
measuring a second optical absorbance A2 of the sample-Karl Fischer mixture,
computing from the difference of said first and second optical absorbances the water content of said sample.

9. The process of claim 8, where the amount of water in said sample is computed according to the expression:

$$\text{water content} = K\left[ A1 - A2 \frac{(V_0 + V_s)}{V_0} \right],$$

where K is a constant.

10. The process of claim 8, where said Karl Fischer solution further includes a halogenated hydrocarbon containing 1-3 carbon atoms partially or fully halogenated, the amount of said halogenated hydrocarbon being at least about 20% by volume of said Karl Fischer solution, and said reducing ion is $SO_2$.

11. The process of claim 10, where said imidazole or its derivatives is present in said Karl Fischer solution in an amount about 0.001-4.5 moles per liter.

12. A process for the colorimetric determination of the water content of a sample using a Karl Fischer reaction, comprising the steps of:
providing a sealed vial containing therein a volume $V_0$ of Karl Fischer solution including $SO_2$, a buffer, iodine in an amount less than 0.005 moles per liter, iodide and a solvent,
measuring a first optical absorbance A1 of said Karl Fischer solution in said sealed vial,
puncturing the seal of said vial by injecting therethrough a sample volume $V_S$ of unknown water content into said sealed vial, to produce a mixture of said sample and said Karl Fischer solution,
measuring a second optical absorbance A2 of said mixture including said sample and said Karl Fischer solution, and
computing the amount of water in said sample from the difference of said first and second optical absorbances.

13. The method of claim 12, where the amount of water in said sample is computed by the expression $$\text{water content} = K\left[ A1 - A2 \frac{(V_0 + V_s)}{V_0} \right],$$

where K is a constant.

14. The method of claim 12, where said solvent includes a halogenated hydrocarbon containing 1-3 carbon atoms partially or fully halogenated, where the halogen is selected from the group consisting of chlorine, bromine, and iodine, said halogenated hydrocarbon being present in said solvent in a concentration greater than about 20% by volume.

15. The method of claim 14, where said halogenated hydrocarbon is chloroform.

16. The method of claim 14, where said halogenated hydrocarbon is selected from the group consisting of chloroform, bromoform, 1,2 dichloroethane, trichloroethylene, and iodomethane.

17. The method of claim 12, where said buffer includes imidazole or its derivatives in a concentration of about 0.001-4.5 moles per liter.

18. A process for the colorimetric determination of the water content of a sample using a Karl Fischer reaction, comprising the steps of:
providing a sealed vial containing therein a volume of Karl Fischer solution including $SO_2$, a buffer, iodine, iodide, and a solvent, measuring a first optical absorbance of said Karl Fischer solution in said sealed vial, adding a sample volume of unknown water content to said sealed vial, measuring a second optical absorbance of a mixture including said sample and said Karl Fischer solution, and computing the amount of water in said sample from the difference of said first and second optical absorbances, where said sealed vial has a portion thereof enclosed in an elastic enclosing means wherein said sample is introduced into said vial by breaking said vial into discrete parts held together by said elastic enclosing means and piercing the elastic enclosing means with a syringe needle, said sample being introduced into said vial in a fixed amount from said syringe.

19. A process for the colorimetric determination of the water content of a sample using a Karl Fischer reaction, comprising the steps of:

providing a sealed vial containing a Karl Fischer solution including $SO_2$, a buffer including imidazole or its derivatives, iodine in an amount less than about 0.005 moles per liter, iodide, and a solvent including a halogenated hydrocarbon in an amount at least about 20% by volume, measuring a first optical absorbance of said Karl Fischer solution in said sealed vial, breaking the seal of said vial by injecting therethrough a sample of unknown water content to produce a mixture including said Karl Fischer solution and said sample, measuring a second optical absorbance of said mixture including said sample and said Karl Fischer solution, and computing the amount of water in said sample from the difference of said first and second optical absorbances.

20. The process of claim 19, in which said imidazole or its derivatives is present in an amount of about 0.001–4.5 moles per liter.

21. The process of claim 20, where said solvent includes an alcohol.

22. An optically transparent, sealed glass vial containing a Karl Fischer solution for the colorimetric analysis of the water content of a sample introduced therein, said solution including $SO_2$, iodine in a concentration less than about 0.005 moles per liter, imidazole or its derivatives, iodide, and a solvent, the ratio of concentrations of $SO_2$: imidazole or its derivatives being in the range of about 0.95:1–0.005:1.

23. The sealed glass vial of claim 22, where the ratio of concentrations of $SO_2$: iodine is in the range of about 3:1–3:0.001.

24. The sealed glass vial of claim 22, where the ratio of concentrations iodide: iodine is in the range of about 3:0.95–3:0.0001.

25. An optically transparent, sealed vial containing a Karl Fischer solution for the colorimetric analysis of the water content of a sample introduced therein, said solution including $SO_2$, iodine in a concentration less than 0.005 moles per liter, a buffer, iodide in a concentration at least about 0.002 moles per liter, and a solvent.

26. The sealed glass vial of claim 25, wherein a vacuum is present in said vial.

27. The sealed vial of claim 25, where said sealed vial is an all glass vial.

28. A process for the colorimetric determination of water content of a sample, comprising the steps of:

providing a sealed vial having a section of approximately constant diameter including a scoremark and an elastic enclosure means surrounding said section in the vicinity of said scoremark, said vial being sealed and containing a Karl Fischer solution therein of known volume $V_0$, said solution including a reducing ion, alcohol, a buffer, iodine in an amount less than about 0.005 moles per liter and iodide, breaking said vial along said scoremark to produce discrete pieces, said vial being substantially sealed from the atmosphere by said elastic enclosure means, adding a sample of known volume $V_S$ of unknown water content into said vial, said sample being injected into said vial through the seal of said elastic enclosure means, mixing said sample and said Karl Fischer solution in said vial, said elastic enclosure means substantially preventing the contents of said vial from being exposed to the atmosphere, and observing any change in color that occurs when said sample is added as an indication of the water content of said sample.

29. The process of claim 28, in which the volume $V_S$ of said sample added to said vial is sufficient to make the sample-K.F. reagent mixture substantially colorless.

30. The process of claim 28, where said buffer is comprised of imidazole or its derivatives.

31. An optically transparent sealed vial containing a colorimetric Karl Fischer solution for colorimetric analysis of the water content of a sample injected through the seal of said vial, said solution including $SO_2$, iodine in a concentration less than 0.005 moles per liter, imidazole or its derivatives, iodide and a solvent.

* * * * *